(12) United States Patent
Cho et al.

(10) Patent No.: US 6,417,635 B2
(45) Date of Patent: Jul. 9, 2002

(54) APPARATUS AND METHOD FOR ELECTRICALLY DISPOSING OF HYPODERMIC NEEDLE

(75) Inventors: Gil-wan Cho; Kyung-nam Kim, both of Seoul (KR)

(73) Assignee: Intermagic Corporation, Seoul (KR)

( * ) Notice: Subject to any disclaimer, the term of this patent is extended or adjusted under 35 U.S.C. 154(b) by 0 days.

(21) Appl. No.: 09/777,887

(22) Filed: Feb. 7, 2001

(30) Foreign Application Priority Data

Aug. 11, 2000 (KR) ........................................ 2000-46701
Nov. 8, 2000 (KR) ........................................ 2000-66200

(51) Int. Cl.[7] ........................... A61L 11/00; B23K 11/22
(52) U.S. Cl. ......................... 318/445; 318/696; 219/68
(58) Field of Search .................. 318/685, 696, 318/445; 219/68

(56) References Cited

U.S. PATENT DOCUMENTS

| | | | | |
|---|---|---|---|---|
| 4,628,169 A | * | 12/1986 | Ching-Lung | 219/68 |
| 4,877,934 A | * | 10/1989 | Spinello | 219/68 |
| 5,076,178 A | * | 12/1991 | Kohl et al. | 110/250 |
| 5,329,087 A | * | 7/1994 | Kohl et al. | 219/68 |
| 5,468,928 A | * | 11/1995 | Yelvington | 219/68 |
| 5,540,416 A | * | 7/1996 | Huang | 266/200 |
| 5,548,095 A | * | 8/1996 | Cornell | 219/68 |
| 5,637,238 A | * | 6/1997 | Truesdale et al. | 219/68 |
| 5,868,709 A | * | 2/1999 | Champion et al. | 219/68 X |

* cited by examiner

*Primary Examiner*—Bentsu Ro
(74) *Attorney, Agent, or Firm*—Dickstein Shapiro Morin & Oshinsky, LLP

(57) ABSTRACT

An apparatus and method for electrically disposing of a hypodermic needle, which provide electric power to the hypodermic needle to generate heat and eliminate the needle with the heat, comprising: an insertion hole through which the hypodermic needle is inserted; an electrode plate which comes into contact with the hypodermic needle being inserted, to provide it with electric power; an electrode wing which comes into contact with the hypodermic needle to melt and eliminate it, the electrode wing having a polarity opposite to that of the electrode plate; a motor for turning the electrode wing; and a controller for controlling the motor.

8 Claims, 5 Drawing Sheets

APPARATUS AND METHOD FOR ELECTRICALLY DISPOSING OF HYPODERMIC NEEDLE

BACKGROUND OF THE INVENTION

1. Field of the Invention

The present invention relates to an apparatus and method for electrically disposing of a hypodermic needle, more specifically, to an apparatus and method for electrically disposing of a hypodermic needle by allowing for a hypodermic needle to be disposed of with electric power generated heat, thereby melting the needle and eliminating it.

2. Description of the Related Art

A used hypodermic needle may be infected with germs, such that it would transfer the germs to people if not properly disposed of. Accordingly, a used and infected hypodermic needle should be disposed of by separate collection and sterilization or by eliminating with heat and melting it. Electric energy can be employed in order to eliminate a used hypodermic needle by making it molten. In this method, the application of a voltage to a hypodermic needle made of metal results in the generation of heat due to the resistance of the metal needle. Thus, when sufficiently high voltage is supplied to the hypodermic needle, the needle becomes molten due to the heat generated.

The conventional apparatus for electrically melting and eliminating a hypodermic needle is described below with reference to FIG. 1.

A conventional voltage supply apparatus for eliminating a used hypodermic needle includes two electrode plates 12 and 14 that supplies voltage to the hypodermic needle 10. These two electrode plates 12 and 14 are connected to a power supply having opposite polarities (+) and (−), respectively. After the power supply is turned ON, the inserted hypodermic needle 10 simultaneously comes into contact with the two electrode plates 12 and 14, and the power is applied to the needle 10 through the electrode plates 12 and 14. Here, the hypodermic needle itself serves as a resistor so that heat generates in the needle due to the supplied power. Thereafter, this heat melts the hypodermic needle 10.

The above-described hypodermic needle elimination method has the following problems.

As the hypodermic needle to be disposed of melts, a user senses the melting state by sight or by feeling the hypodermic injector more, and pushed the needle grasped in his hand further into the apparatus little by little. Applying excessively strong pressure to the hypodermic injector or needle causes problems in the apparatus. On the other hand, too little pressure does not allow the needle to come into contact with the electrode plates. Furthermore, an inappropriate insertion angle of the needle generates multiple sparks between the electrode plates.

SUMMARY OF THE INVENTION

It is, therefore, an object of the present invention to provide an apparatus and method for electrically disposing of a hypodermic needle in which, once a hypodermic needle is inserted, the needle is used and then eliminated through a full automatic operation.

Another object of the present invention is to provide an apparatus and method for electrically disposing of a hypodermic needle, which allow a needle elimination operation to be smoothly performed even if the insertion angle of the needle is varied.

To accomplish the objects of the present invention, there is provided an apparatus for electrically disposing of a hypodermic needle, comprising: an insertion hole through which the hypodermic needle is inserted; an electrode plate which comes into contact with the hypodermic needle being inserted, to provide it with electric power; an electrode wing which comes into contact with the hypodermic needle to melt and eliminate it, the electrode wing having a polarity opposite to that of the electrode plate; a motor for turning the electrode wing; and a controller for controlling the motor.

According to a preferred embodiment of the invention, the apparatus further comprises a display for providing information about elimination state of the needle, power state, operation error, etc., and a fan for spreading heat and removing reek, and the electrode wing has a protrusion and depression formed thereon such that it comes into contact with the hypodermic needle.

The electrode plate may have a spring means for allowing the electrode plate and the hypodermic needle to come into contact with each other closely. The motor may be a stepping motor. The apparatus may further comprise a sensor for sensing the needle being inserted through the insertion hole and delivering it to the controller.

To accomplish the objects of the invention, there is also provided a method for electrically disposing of a hypodermic needle, comprising the steps of: sensing if the hypodermic needle is inserted to come into contact with an electrode plate; upon sensing of insertion of the hypodermic needle, a controller controlling a motor to drive it; the motor turning an electrode wing to allow it to come into contact with the needle, to thereby heat and eliminate the needle, the electrode wing having a polarity opposite to that of the electrode plate; the controller controlling the motor by an electric signal sent by a closed circuit consisting of the hypodermic needle, the electrode plate and the electrode wing; and, upon the electrode wing reaching a predetermined position, the controller controlling the motor to reverse the electrode wing to return it to its initial position.

According to a preferred embodiment of the invention, the step of controlling the motor by the controller using the electric signal comprises the substeps of: the controller detecting the potential of the electrode wing at the moment when the electrode wing comes into contact with the needle; when the potential is 0V, the controller controlling the motor to stop the electrode wing and to vibrate it; and when the potential is not equal to 0V, the controller controlling the motor to turn the electrode wing such that the electrode wing comes into contact with the hypodermic needle.

The step of detecting the potential of the electrode wing by the controller comprises the substeps of: inputting the potential of the electrode wing into an operational amplifier; the controller controlling the motor to stop revolution of the electrode wing when the output of the operational amplifier is LOW; and the controller controlling the motor to turn the electrode wing when the output of the operational amplifier is HIGH.

DETAILED DESCRIPTION OF THE PREFERRED EMBODIMENT

Reference will now be made in detail to the preferred embodiments of the present invention, examples of which are illustrated in the attached drawings.

Figure 1:
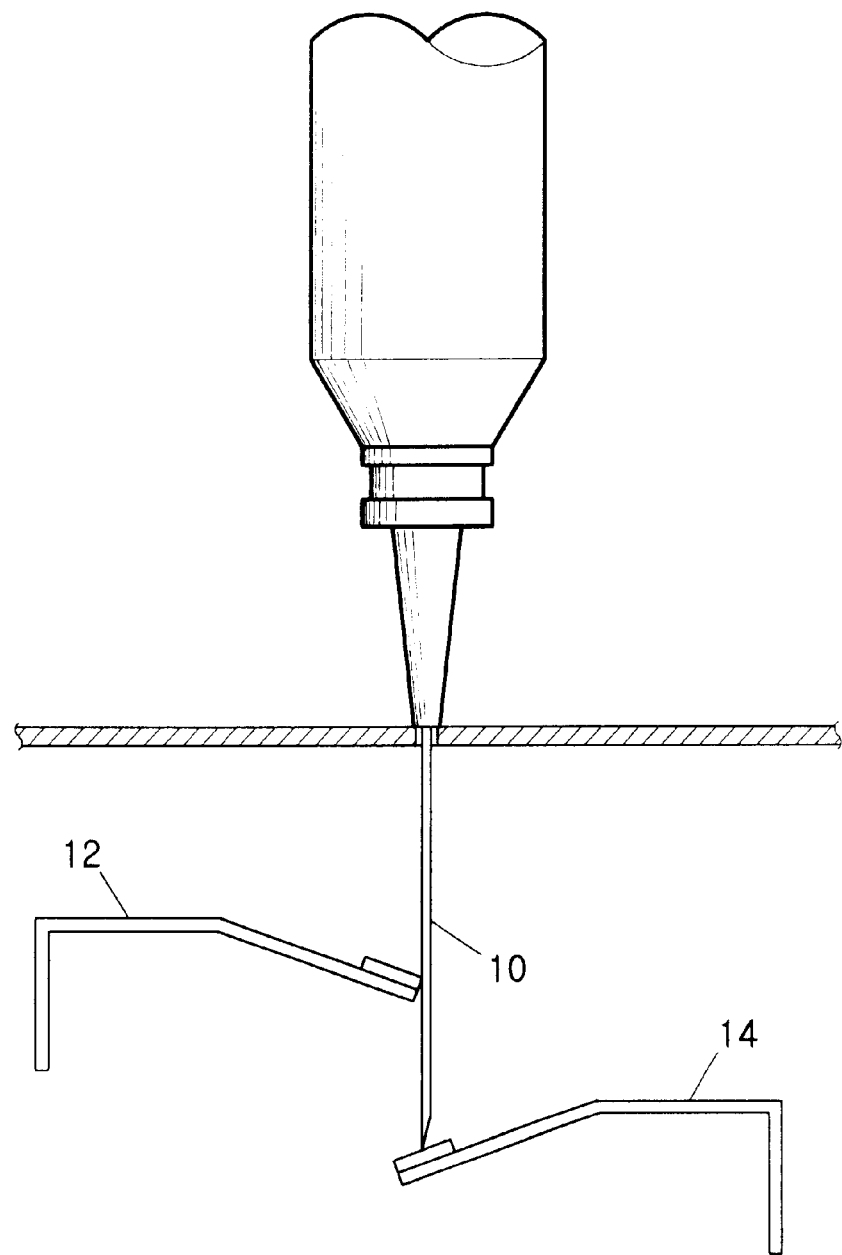
FIG. 1 illustrates a conventional apparatus for disposing of a hypodermic needle.
Figure 2:
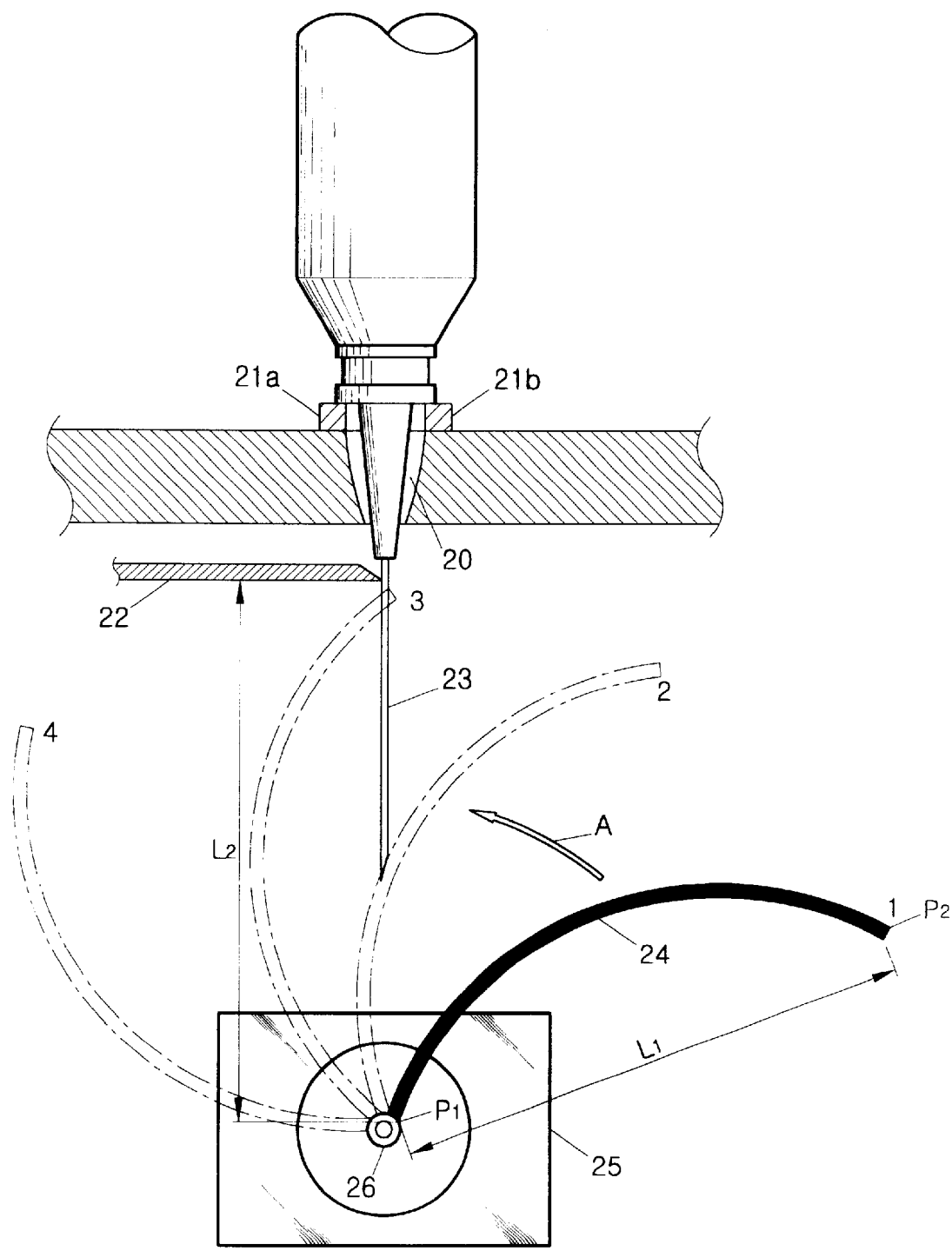
FIG. 2 is a front view of an apparatus for disposing of a hypodermic needle according to the present invention.

FIG. 2 illustrates the configuration of an apparatus for disposing of a hypodermic needle according to the present invention. Referring to FIG. 2, the hypodermic needle elimination apparatus has an insertion hole 20 through which a hypodermic needle 23 is inserted. An electrode plate 22, located beneath the insertion hole 20, comes into contact with the inserted needle 23 supplying electric power thereto. Beneath the electrode plate 22, an electrode wing 24 turns such that it comes into contact with the hypodermic needle 23 to provide electric power thereto. The electrode wing 24 has a polarity opposite to that of the electrode plate 22. One end of the electrode wing 24 is connected to a motor 25 by a driving shaft 26 such that the electrode wing 24 turns on the driving shaft 26 by the motor 25 in the direction of the arrow A in FIG. 2. In addition, supports 21a and 21b are located around the insertion hole 23. The supports 21a and 21b control the insertion depth of the hypodermic needle 23 allowing the needle 23 to be inserted into the apparatus to come in contact with the electrode plate 22.

The insertion hole 20 has a width that becomes narrower as the needle continues to go in. Accordingly, by simply inserting the hypodermic needle 23 into the insertion hole 20, the needle can be inserted smoothly into the apparatus by climbing down the inner wall of the insertion hole 20. Contact of the electrode wing 24 and hypodermic needle 23 is secured even if the location of the inserted hypodermic needle 23 changes slightly in the apparatus because the electrode wing 24 has a specific width. A protrusion and depression on the surface of the electrode wing 24 improves the contact resistance of the electrode wing 24 and needle 23.

Figure 3:
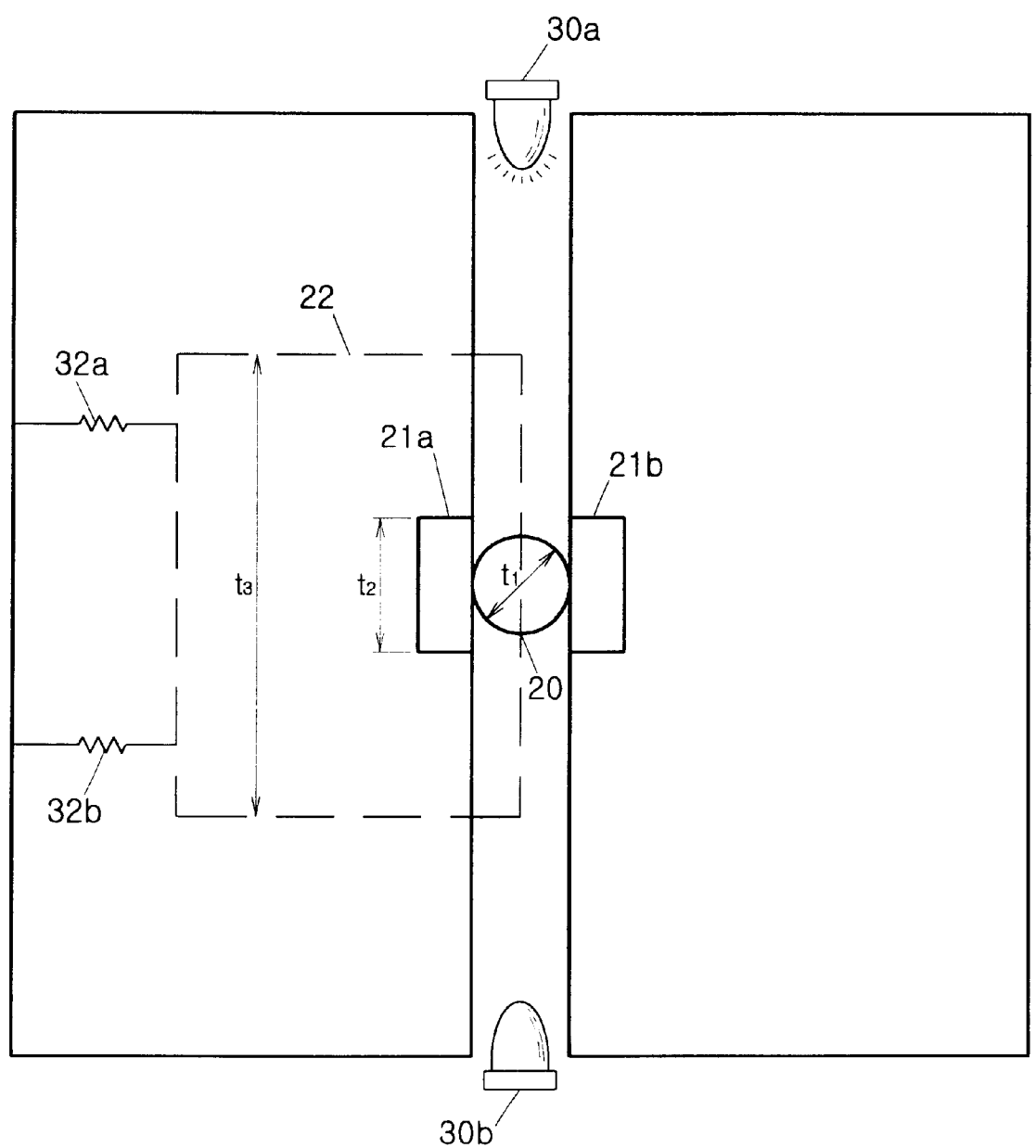
FIG. 3 is a plan view of the apparatus for disposing of a hypodermic needle according to the present invention.

The electrode plate 22 has springs 32a and 32b (referring to FIG. 3). These springs push the electrode plate 22 toward the needle 23 allowing the electrode plate and needle to come into tight contact with each other. As the electrode wing 24 turns toward the electrode plate 22 in the direction of arrow A, it pushes the needle 23 toward the electrode plate 22 to prevent the needle from being separated from the electrode plate 22.

One end P1 of the electrode wing 24 is combined with the driving shaft 26 of the motor 25. The electrode wing 24 which is a plate having a predetermined width is curved in a manner so that the bulging portion corresponds to the turning direction. A straight distance L1 between the driving shaft 26 and the other end P2 of the electrode wing 24 is shorter than the distance L2 between the driving shaft 26 and the electrode plate 22. Preferably, L1 must be minimally shorter smaller than L2 such that the other end P2 of the electrode wing does not come into contact with the electrode plate 22. The electrode wing 24 is preferably made from chrome. As chrome material does not attract other materials, it can prevent by-products generated when the hypodermic needle is disposed of from being attached onto the electrode wing 24 to obstacle supply of electric power thereto.

FIG. 3 is a plan view of the apparatus for disposing of the hypodermic needle according to the present invention. Referring to FIG. 3, the width t2 of the supports 21a and 21b is wider than the diameter t1 of the insertion hole 20 so that the supports can hold the hypodermic needle even if the position of the needle changes slightly. The width t3 of the electrode plate 22 is also larger than the diameter of the insertion hole so that the electrode plate can come into contact with the hypodermic needle. The apparatus for disposing of the hypodermic needle also includes a sensor consisting of a light emitting part 30a and a light receiving part 30b, respectively located at both sides of the insertion hole 20, to sense the insertion state of the needle as it moves into the apparatus. This sensor, which may be configured of an optical sensor, detects when the hypodermic needle is introduced into the apparatus to allow the apparatus to start the needle elimination work. When the inserted needle 23 comes in contact with the electrode plate 22, the electrode plate 22 is pushed toward the inserted needle by the elasticity of the springs 32a and 32b attached thereto. Thus, contact of the electrode plate 22 and needle 23 is constantly secured.

When a user inserts the hypodermic needle 23 into the apparatus through the insertion hole 20, the needle 23 comes into contact with the electrode plate 22. As the sensors 30a and 30b sense the insertion state of the needle, the operation of disposing of the needle 23 starts automatically. Then, electric power is supplied from the power supply to the hypodermic needle 23 through the electrode plate 22. The electrode plate 22 is pushed by the springs 32a and 32b to come in close contact with the hypodermic needle.

The electrode wing 24 is initially positioned at a location 1 of FIG. 2 and turns on the driving shaft 26 under the operation of the motor 25 to arrive at a location 2, coming into contact with the tip of the hypodermic needle 23. When the electrode wing 24 is in contact with the hypodermic needle 23, a closed circuit is created so that current flows through the needle because the electrode wing 24 is supplied with power from the power supply, having a polarity opposite to that of the electrode plate 22. Due to the current flowing through the needle 23, heat is generated caused by the resistance of the hypodermic needle itself. With a sufficiently high supply power, a large enough amount of heat is generated, melting the needle 23 and eliminating it. Here, since a larger amount of heat is created at the portion where the electrode wing 24 and hypodermic needle 23 come into contact with each other than any other portion of the needle, the contact portion melts faster than the other portions.

The surface of the electrode wing 24 may have a prominence and depression formed thereon in order to increase the contact resistance between the electrode wing 24 and hypodermic needle 23. If such is the case, the surface area of the electrode wing 24, which comes into contact with the needle 23, becomes smaller to raise contact resistance, thereby easily melting the hypodermic needle with a smaller amount of power.

When the contact portion between the needle 23 and electrode wing 24 moves from the lower part of the needle to its upper part so that the electrode wing 24 reaches position 3 of FIG. 2, the hypodermic needle is completely eliminated. When the electrode wing 24 continuously turns to pass the hypodermic injector to arrive at a position 4 in FIG. 2, the motor is reversed to return the electrode wing 24 to the initial position 1 where the electrode wing waits for the next operation. That is, the operation sequence of the electrode wing 24 is position 1→2→3→4→3→2→1. The above construction in which the electrode wing is returned to its initial position upon total elimination of the hypodermic needle is for minimizing the operation space to effectively use the space inside the case of the apparatus. The motor 25 is a stepping motor configuration with easily controllable revolution angles and speeds.

Figure 4:
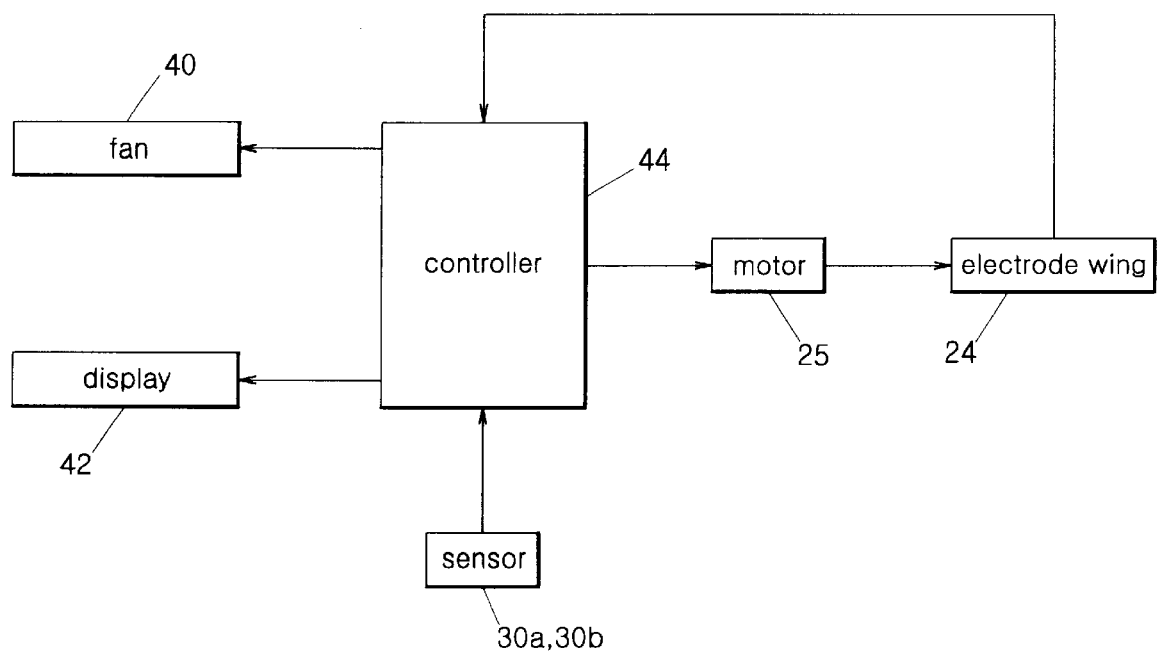
FIG. 4 is a block diagram of the apparatus for disposing of a hypodermic needle according to the present invention.

The operation of the apparatus for disposing of the hypodermic needle is automatically performed under the control of a controller, which is shown in FIG. 4. When the hypodermic needle 23 is inserted into the apparatus, the sensor 46 detects the needle and sends an electric signal to the controller 44. The controller 44 receives this signal to drive the motor 25 to turn the electrode wing 24. When the electrode wing 24 comes in contact with the tip of the needle 23 according to the operation of the motor 25, the controller 44 also forces the motor 25 to stop. The electrode plate 22 and electrode wing 24 which have polarities opposite to each other form a closed circuit to have the current flow through the needle 23. The contact portion between the needle 23 and electrode wing 24 generates heat due to the contact resistance between them. This heat melts the contact portion to eliminate it.

Elimination of the contact portion between the needle 23 and electrode wing 24 isolates the two from each other. Then, the controller 44 detects this isolation state and forces the motor 25 to revolve again, thereby allowing the electrode wing 24 to come into contact with the hypodermic needle. When the controller 44 detects the contact state, it forces the motor 25 to stop. This procedure is repeated until the hypodermic needle is completely eliminated. Upon the electrode wing 24 arriving at the final position (4 in FIG. 2), the controller 44 forces the motor 25 to reverse the electrode wing, returning it to the initial position.

In addition, the controller 44 can force the motor 25 to vibrate the electrode wing 24 connected to the driving shaft. That is, controller 44 forces the revolution direction and angle of the motor 25 allowing the electrode wing 24 to reciprocate at a high speed within a minute angle, while remaining in contact with the hypodermic needle, thereby vibrating the electrode wing 24. Vibration of the electrode wing 24 increases the contact resistance between the electrode wing 24 and needle 23 so that the needle can be easily melted and the contact portion between the electrode wing and needle, molten by heat, can be detached from the needle as soon as it melts.

Meanwhile, the controller 44 drives a fan 40 to spread heat generated in the apparatus and removes smoke or oders created when the needle is eliminated. In addition, the controller 44 controls a display 42 to inform the user of charging and discharging states of a battery supplying power to the motor 25, the starting of the needle elimination, process state, generation of error, etc.

Figure 5:
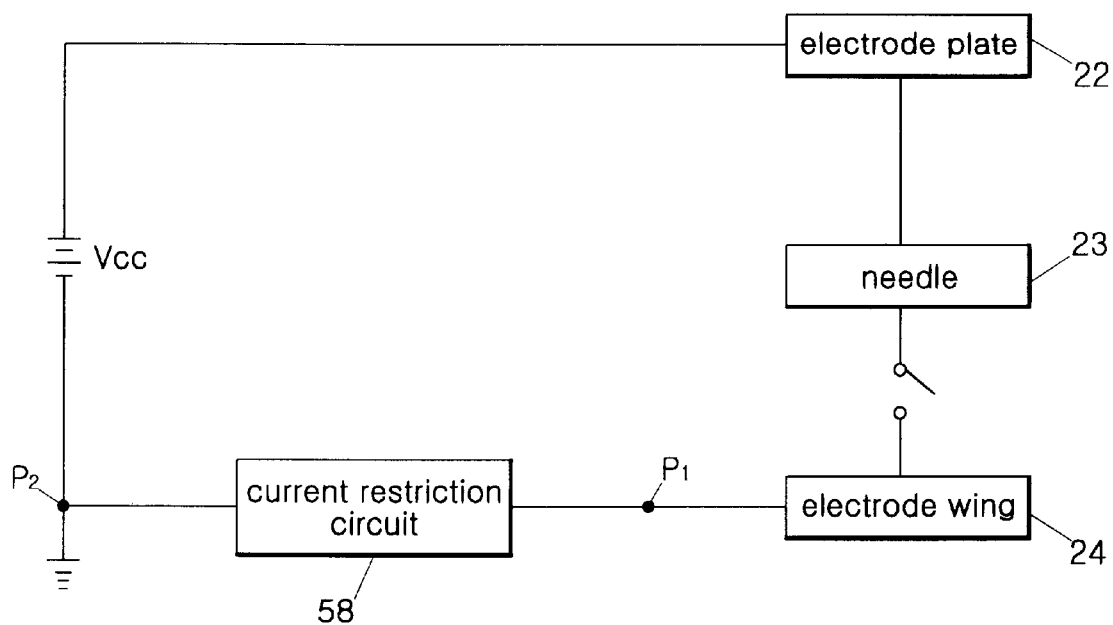
FIG. 5 is an equivalent circuit diagram of the apparatus for disposing of a hypodermic needle according to the present invention.

FIG. 5 illustrates an electric circuit consisting of the electrode plate, hypodermic needle and electrode wing in order to explain a method for judging by the controller whether the hypodermic needle comes into contact with the electrode wing 24 or not. Referring to FIG. 5, the electrode plate 22, hypodermic needle 23 and electrode wing 24 are connected in series, and the needle 23 and electrode wing 24 have a switch in between. This switch indicates whether the electrode wing 24 comes into contact with the hypodermic needle 23 or not. Further, included is a current restriction circuit 58 inserted serially in order to prevent overcurrent from flowing through the closed circuit configured of the electrode plate 22, needle 23 and electrode wing 24. A node P2 is grounded.

When the switch is turned off while the circuit is supplied with voltage Vcc, the potential of the node P1 becomes 0V. When the switch is turned on, however, the potential of the node P1 becomes Vp($\neq$0). That is, the potential of the node P1 varies between 0V and Vp($\neq$0) depending on the state of the switch. When the potential of the node P1 is applied to an operational amplifier and the output of the operational amplifier becomes LOW or HIGH depending on the potential value, the controller detects this to judge if the electrode wing 24 is in contact with the hypodermic needle 23 or not. For example, in a case where an operational amplifier is employed, which generates an output LOW when the electrode wing 24 is isolated from the needle 23, i.e., when the potential of the node P1 is 0V, but generates an output HIGH when the electrode wing 24 is in contact with the needle 23, i.e., when the potential of the node P1 is Vp, the controller 44 forces the motor to turn the electrode wing 24 allowing it to come into contact with the needle 23 in case of the output LOW whereas it forces the motor to stop the revolution of electrode wing 24 to maintain the contact between the electrode wing 24 and needle 23 in case of the output HIGH.

As described above, according to the present invention, the sensor senses the inserted hypodermic needle inserted and the controller detects the state of the needle to operate the motor so that, once the needle, it is completely eliminated through fully automatic operation.

What is claimed is:

1. An apparatus for electrically disposing of a hypodermic needle, comprising:
    an insertion hole through which the hypodermic needle is inserted;
    an electrode plate which comes in contact with the inserted hypodermic needle and provides the inserted hypodermic needle with electric power;
    an electrode wing which comes in contact with the inserted hypodermic needle and melts and eliminates the needle, the electrode wing having a polarity opposite to that of the electrode plate;
    a motor for turning the electrode wing;
    a controller for controlling the motor; and
    a spring means for allowing the electrode plate and the inserted needle to come in close contact with each other.

2. The apparatus as claimed in claim 1, further comprising a display for providing information about an elimination state of the needle, a power state and operation error, and a fan for spreading heat and removing odors, wherein the electrode wing has a protrusion and depression formed thereon such that it comes in contact with the hypodermic needle.

3. The apparatus as claimed in claims 1 or 2, wherein the motor is a stepping motor.

4. The apparatus as claimed in claims 1 or 2, further comprising a sensor for sensing a signal indicating that the needle is being inserted through the insertion hole and delivering said signal to the controller.

5. An apparatus for electrically disposing of a hypodermic needle, comprising:
    an insertion hole through which the hypodermic needle is inserted;
    an electrode plate which comes in contact with the inserted hypodermic needle and provides the inserted hypodermic needle with electric power;
    an electrode wing which comes in contact with the inserted hypodermic needle and melts and eliminates the needle, the electrode wing having a polarity opposite to that of the electrode plate;
    a motor for turning the electrode wing;

a controller for controlling the motor; and a sensor for sensing a signal indicating that the needle is being inserted through the insertion hole and delivering said signal to the controller.

6. A method for electrically disposing of a hypodermic needle, comprising the steps of:

sensing if the hypodermic needle is inserted to come into contact with an electrode plate;

upon sensing of insertion of the hypodermic needle, controlling a motor by a controller to drive it;

turning an electrode wing by the motor to allow it to come into contact with the needle, to thereby heat and eliminate the needle, the electrode wing having a polarity opposite to that of the electrode plate;

controlling the motor by the controller with an electric signal sent by a closed circuit consisting of the hypodermic needle, the electrode plate and the electrode wing; and upon the electrode wing reaching a predetermined position, controlling the motor by the controller to reverse the electrode wing to return it to its initial position.

7. The method as claimed in claim 6, wherein the step of controlling the motor by the controller using the electric signal comprises the substeps of:

detecting the potential of the electrode wing by the controller at the moment when the electrode wing comes into contact with the needle;

when the potential is 0V, controlling the motor by the controller to stop the electrode wing and to vibrate it; and when the potential is not equal to 0V, controlling the motor by the controller to turn the electrode wing such that the electrode wing comes into contact with the hypodermic needle.

8. The method as claimed in claim 7, wherein the step of detecting the potential of the electrode wing by the controller comprises the substeps of:

inputting the potential of the electrode wing into an operational amplifier;

controlling the motor by the controller to stop revolution of the electrode wing when the output of the operation amplifier is LOW; and controlling the motor by the controller to turn the electrode wing when the output of the operational amplifier is HIGH.

* * * * *